United States Patent
Paul et al.

(10) Patent No.: US 10,551,352 B2
(45) Date of Patent: Feb. 4, 2020

(54) METHOD FOR DETECTING DEFECTS IN A MATERIAL BY ULTRASOUNDS

(71) Applicant: Electricite de France, Paris (FR)

(72) Inventors: Nicolas Paul, Montreuil (FR); Paul Kassis, Paris (FR)

(73) Assignee: Electricite de France, Paris (FR)

( * ) Notice: Subject to any disclaimer, the term of this patent is extended or adjusted under 35 U.S.C. 154(b) by 0 days.

(21) Appl. No.: 16/304,119

(22) PCT Filed: May 24, 2017

(86) PCT No.: PCT/FR2017/051282
§ 371 (c)(1),
(2) Date: Nov. 21, 2018

(87) PCT Pub. No.: WO2017/203166
PCT Pub. Date: Nov. 30, 2017

(65) Prior Publication Data
US 2019/0339233 A1    Nov. 7, 2019

(30) Foreign Application Priority Data
May 25, 2016 (FR) ..................... 16 54708

(51) Int. Cl.
*G01N 29/07* (2006.01)
*G01N 29/04* (2006.01)
(Continued)

(52) U.S. Cl.
CPC .......... *G01N 29/07* (2013.01); *G01N 29/043* (2013.01); *G01N 29/265* (2013.01); *G01N 29/28* (2013.01);
(Continued)

(58) Field of Classification Search
CPC .... G01N 29/07; G01N 29/043; G01N 29/265; G01N 29/28; G01N 29/4463;
(Continued)

(56) References Cited

U.S. PATENT DOCUMENTS

| 5,932,807 A | 8/1999 | Mallart |
| 2007/0006651 A1 | 1/2007 | Kruger et al. |

FOREIGN PATENT DOCUMENTS

| DE | 202013105253 U1 | 2/2014 |
| EP | 0330735 A2 | 9/1989 |

(Continued)

OTHER PUBLICATIONS

Preliminary Research Report and Written Opinion received for French Application No. 1654708, dated Feb. 9, 2017, 9 pages (1 page of French Translation Cover Sheet and 8 pages of original document).

(Continued)

*Primary Examiner* — Tarun Sinha
(74) *Attorney, Agent, or Firm* — Lerner, David, Littenberg, Krumholz & Mentlik, LLP (57) ABSTRACT

The invention concerns a method for ultrasounds detection of defects in a material, including the following steps:
emission of ultrasounds from an ultrasonic emitting transducer positioned against to the material at an emission position,
acquisition, by an ultrasonic receiving transducer placed against the material at the reception position, of at least one time signal,
for each measurement position, determination of a normalisation term from the values taken by the time signal during an initial portion of the measurement duration corresponding to the reception of ultrasonic waves propagated at the surface of the material;

(Continued)

for each measurement position, normalisation of the time signal over the measurement duration using the normalisation term to obtain a normalised time signal, processing of normalised time signals for different measurement positions to detect defects in the material.

10 Claims, 5 Drawing Sheets

(51) Int. Cl.
    *G01N 29/265*    (2006.01)
    *G01N 29/28*     (2006.01)
    *G01N 29/44*     (2006.01)

(52) U.S. Cl.
    CPC ..... *G01N 29/4463* (2013.01); *G01N 29/4472* (2013.01); *G01N 2291/011* (2013.01); *G01N 2291/0234* (2013.01); *G01N 2291/0289* (2013.01); *G01N 2291/102* (2013.01); *G01N 2291/2634* (2013.01)

(58) Field of Classification Search
    CPC ......... G01N 29/4472; G01N 2291/011; G01N 2291/0234; G01N 2291/0289; G01N 2291/102; G01N 2291/2634
    USPC ........................................................ 73/579
    See application file for complete search history.

(56) References Cited

FOREIGN PATENT DOCUMENTS

JP       2009-270824 A     11/2009
JP        2009270824 A  *  11/2009

OTHER PUBLICATIONS

International Search Report and Written Opinion received for PCT Patent Application No. PCT/FR2017/051282, dated Sep. 4, 2017, 21 pages (10 pages of English Translation and 11 pages of Original Document).

International Preliminary Report on Patentability received for PCT Patent Application No. PCT/FR2017/051282, dated Dec. 6, 2018, 17 pages (9 pages of English Translation and 8 pages of Original Document).

* cited by examiner

METHOD FOR DETECTING DEFECTS IN A MATERIAL BY ULTRASOUNDS

GENERAL TECHNICAL FIELD AND CONTEXT OF THE INVENTION

The present invention concerns the non-destructive testing of materials, and more specifically detection and characterisation by ultrasounds of defects in a material.

Ultrasounds are commonly used to implement non-destructive testing of materials. To do so, an ultrasonic probe is placed on the surface of the material which is to be examined, which emits ultrasonic waves in the material. These waves are transformed and propagated in the material in different directions depending on its structure. The transducer receives a proportion of these propagated waves, and analysis of them enables any defects in the material to be detected.

Patent application US 2007/0006651 A1 discloses a method for non-destructive testing by means of ultrasonic waves, based on a comparison of the amplitude of the frequency spectrum of a selection of the signal with a reference amplitude. This application mentions the possibility of making measurements at different positions, and mentions combining these measurements to obtain an average measurement signal in the spatial sense.

Similarly, application JP 2009-270824 A discloses a method for detecting and estimating the size of a defect from signals transmitted and received by an ultrasonic transmitter-receiver moving over the surface of a material. The defect's characterisation is determined on the basis of the strength of the measured signal. The signal is normalised to reduce the value of the signal to 1 when there is no defect, by dividing the signals obtained by a reference value which equates to no defects. This reference value is determined beforehand, and the same standardisation is applied to all signals obtained. This is a standard normalisation, like the one applied in document EP 0 330 735 A2.

However, such methods are not entirely satisfactory, and the signal remains impaired by noise. In fact, most of the inspected parts have surface irregularities, such as for example deformations, variations of roughness, surface accidents, or welds (in particular coating), which can lead to appreciable variations of the quality of the acoustic coupling between the probe and the material which is to be inspected. And the quality of this coupling directly influences the measurements made, and therefore the result of the defect detection operation.

In particular, in the case of a heterogeneous material, i.e. a polycrystalline material, the grain size of which is of the order of one ultrasonic wavelength in this material, the phenomenon of ultrasonic wave diffusion by the structure of the material becomes predominant. This diffusion can then lead to the generation of a structure-borne noise, i.e. an ultrasonic signal of non-negligible amplitude received by the probe, with characteristics similar to those which would be transmitted by a wave reflected by a defect. It is then necessary to be able to distinguish finely between the structure-borne noise and any defects. And surface irregularities, through attenuation of the signal amplitudes and the variations which they cause, can hinder this detection.

Figure 1:
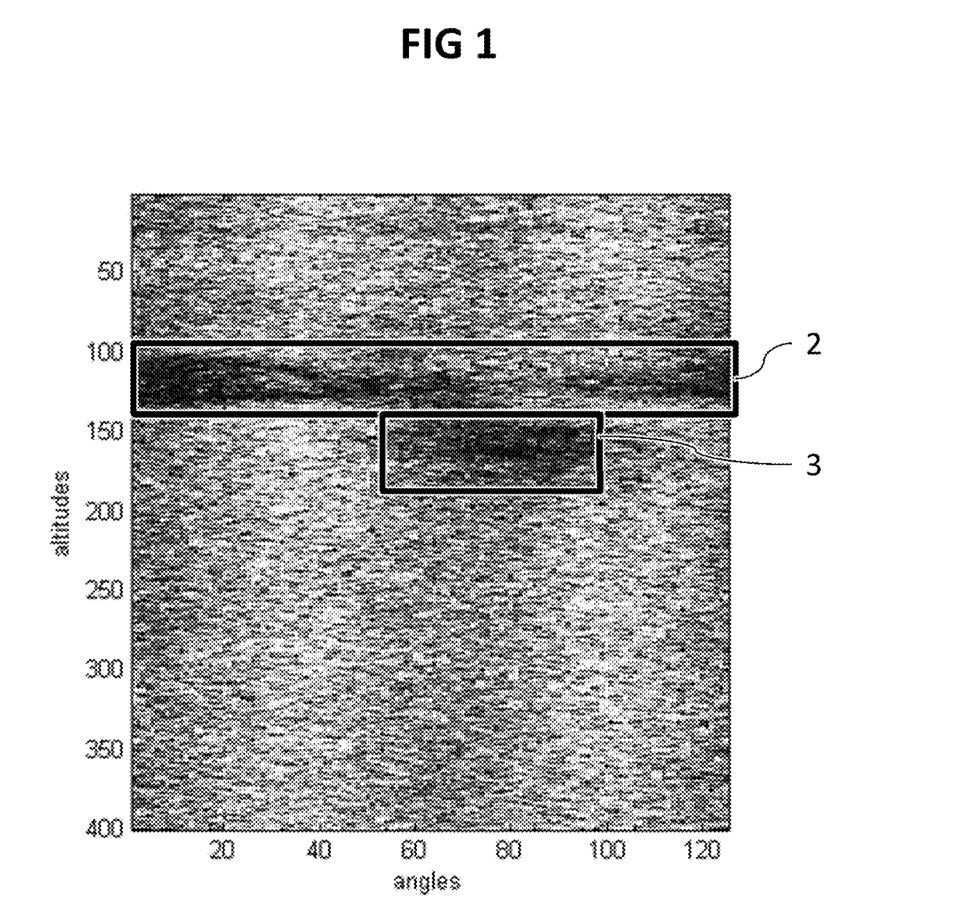
FIG. 1, previously discussed, shows a map illustrating an example of maximum values of the portions of time signals corresponding to the diffraction zones of said time signals for a plurality of measurement positions, revealing a structure-borne noise and coupling faults.

As an illustrative example, FIG. 1 illustrates an example of measurement results obtained on an inner portion of a metal tube, where the shade of the measurement points is brighter the higher the received signal. This is a map of maximum values of the portions of time signals corresponding to the diffraction zones of said time signals, i.e. to the portions representative of the structure-borne noise. In this case the material has no internal defects, and the patterns in the map in FIG. 1 show the structure-borne noise, which is relatively uniform in the material, except for the two anomalies around which two black frames, 2, 3, have been put. In the areas of these anomalies the amplitude of the received signal shows a discontinuity, and is appreciably weaker than for the remainder of the map.

These two discontinuities are due to coupling faults between the probe and the material for these measurement points, caused by surface non-uniformities of the material. These coupling faults give rise, in the measurements, to characteristics similar to those caused by defects inside the material, which confuses defect detection, or makes it impossible.

More generally, the surface irregularities will hinder the interpretations of the signals in several ways:
  the high amplitude variations which they cause can be confused with the presence of a defect;
  due to the weakness of the amplitudes of the emitted or received waves, coupling faults can conceal defects, which are then not detected;
  certain defect detection methods exploit the statistical constancy of the signals, in particular of the structure-borne noise, and the low amplitudes caused by the coupling defects impair these statistics.

PRESENTATION OF THE INVENTION

The purpose of the present invention is to propose a method for detection by ultrasounds of defects in a material which allow a reduction of the influence of the surface irregularities of the material on the coupling between the transducer and the material, the variations of which impair the collected data.

To this end, a method of ultrasounds detection of defects in a material is proposed, comprising the following steps, for a plurality of pairs of emission position and reception position:
  emission of ultrasounds from an ultrasonic emitting transducer placed against the material at an emission position,
  acquisition, by an ultrasonic receiving transducer placed against the material in the reception position corresponding to said emission position, of at least one time signal representative of the amplitude of the ultrasounds propagated in the material over time during a measurement duration at a measurement position, characterised by the fact that the method includes the following steps:
  for each measurement position, determination of a normalisation term of said measurement position using the values taken by the at least one time signal in said measurement position during an initial portion of the measurement duration corresponding to the reception of ultrasonic waves propagated at the surface of the material;
  for each measurement position, normalisation of the time signal at said measurement position in relation to the measurement duration, using the normalisation term of said measurement position, determined on the basis of said time signal at said measurement position, to obtain a normalised time signal,
  processing of normalised time signals for different measurement positions to detect defects in the material.

In particular, the method enables variations of the quality of the probe's sticking on the material to be compensated.

Indeed, determination of the normalisation term at the start of the measurement (not before it), and for each position, enables the normalisation to be adapted to the acquisition configuration of the probe when the measurement is made.

The invention is advantageously completed by the following characteristics, considered singly or in any technically possible combination:

- the ultrasounds are emitted by the ultrasonic emitting transducer during a pulse duration, and the initial portion of the measurement duration is a duration shorter than the propagation time of the ultrasonic waves propagating at the surface of the material between the emission position and the reception position with twice the pulse duration added, where the duration is measured from the start of the pulse;
- the normalisation term is determined from the temporally average power of the values taken by the time signal during the initial portion of the measurement duration corresponding to the reception of ultrasonic waves propagated at the surface of the material;
- for a measurement position, the square of the normalisation term is proportional to the temporally average power of the values taken by the time signal during the initial portion of the measurement duration corresponding to the reception of ultrasonic waves propagated at the surface of the material;
- the method also includes the determination of propagation times between the emission position and the corresponding reception position for the ultrasonic waves, wherein the normalisation term for a measurement position is determined on the basis of the propagation times at different measurement positions.
- the propagation time at a measurement position can be determined by correlating the time signal with a reference signal representative of the reception of an ultrasonic wave;
- for each time grouping of a plurality of propagation time groupings the temporally average power is determined, for measurement positions with a propagation time belonging to said time grouping, of the values taken by the time signal during the initial portion of the measurement duration corresponding to the reception of ultrasonic waves propagated at the surface of the material, and
- the normalisation term of a measurement position is determined from the temporally average powers of the measurement positions of the propagation time grouping corresponding to the propagation time of the measurement position;
- the normalisation term of a measurement position is determined from the temporally average of the average powers of the measurement positions of the propagation time grouping corresponding to the propagation time of the measurement position;
- spatial filtering corresponding to measurement positions distributed over a portion of the surface of the material is used to filter the normalisation term of a measurement position belonging to said surface portion.

The invention also concerns a system for automated data processing including a processor and a memory, appropriate for use in the method according to the invention, and configured to implement at least the following steps:

- for each measurement position, determination of a normalisation term of said measurement position using the values taken by at least the time signal in said measurement position during an initial portion of the measurement duration corresponding to the reception of ultrasonic waves propagated at the surface of the material;
- for each measurement position, normalisation of the time signal at said measurement position in relation to the measurement duration, using the normalisation term of said measurement position, determined on the basis of said time signal at said measurement position, to obtain a normalised time signal,
- processing of normalised time signals for different measurement positions to detect defects in the material.

The invention also concerns a computer program product including program code instructions for execution of the method according to the invention when said program is executed on a computer.

PRESENTATION OF THE FIGURES

The invention will be better understood by means of the following description, which relates to a preferred example embodiment, given as a non-restrictive example and explained with reference to the appended diagrammatic illustrations, where.

DETAILED DESCRIPTION

For purposes of illustration the following description will be made in connection with the non-destructive testing of a tube made of a metal material using ultrasonic transducers. Other types of surface can be inspected, and the invention is not restricted to one tube. Such an acquisition of the measurements of the transducers is commonly made, in particular to implement the technique known as "time of flight diffraction", more commonly known by the acronym TOFD, the data acquisition protocol of which can be implemented for the present invention.

As an example, the frequency of the ultrasonic waves generally used in non-destructive testing can range from 0.1 to 50 MHz, the 2-10 MHz band being the most commonly used one. The wavelength, in this band, is therefore practically comprised, for metals such as steel or aluminium, to be between 3 mm and 0.5 mm.

Figure 2:
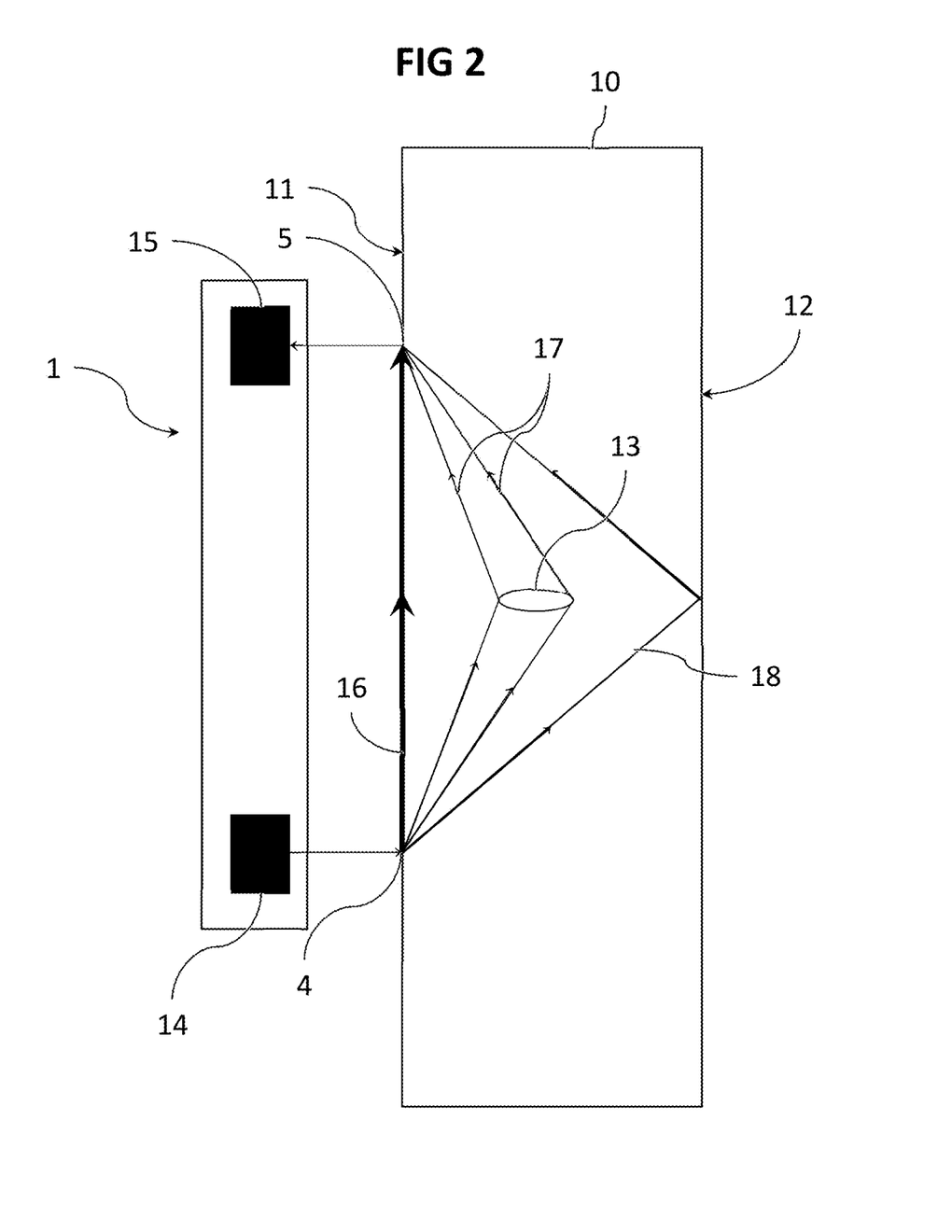
FIG. 2 illustrates the inspection of a tube by an ultrasonic probe.

FIG. 2 illustrates a probe 1 positioned at surface 11 of a tube 10, inspecting tube 10 with defect 13. Emitting transducer 14 and receiving transducer 15 of probe 1 are positioned so as to be aligned in the longitudinal axis of tube 10. They are therefore in a plane parallel to said longitudinal axis of tube 10.

Probe 1 is moved over the surface of the material, and for each measurement position, emits and receives ultrasonic waves the amplitudes of which define the measurement at this measurement position. The measurement position used depends on the approach in question. It can, for example, be the ultrasonic waves' reception position, the emission position, or another position, for example a point of probe 1 which is equidistant between the reception position and the emission position. The definition of the measurement position influences only the geometrical correspondence between the measurement positions and the material. Going from a definition of the measurement position to another simply involves translating the measurements relative to the surface of tube 10.

The data acquired in this manner is defined by a time-dependent amplitude relating to each measurement position. If the measurement position is noted z and the amplitude of the signals x, the time signal received by the probe for measurement position z is noted $x(z,t)$. It should be noted that in the example given here position z is defined by an altitude h and an angle $\theta$. One can also note $x(z,t)=x(h, \theta, t)$. The pitch of the altitude and of the angle depends on the accuracy sought and the dimensional characteristics of the emission and reception beams of the transducers. For example, an altitude pitch of between 0.1 and 2 mm, and an angular pitch of between 1 and 3° can be adopted.

For the measurements, ultrasounds are emitted from the ultrasonic emitting transducer 14 placed against the material. The probe moves over the tube and, for a plurality of emission positions, ultrasonic waves are fired, generally taking the form of a pulse for a short pulse duration. This pulse can, for example, take the form of a rectangle signal or an attenuated sinusoid. The ultrasonic waves emitted by the emitting transducer 14 enter the tube 10 in its inner wall 11, and are then propagated in the material of said tube 10.

For a plurality of pairs of emission position and reception position the method according to the invention also includes the emission of ultrasounds from the ultrasonic emitting transducer 14 placed against the material at an emission position, and the acquisition, by the ultrasonic receiving transducer 15 placed against the material at the reception position corresponding to said emission position, of at least one time signal representative of the amplitude of the ultrasounds propagated in the material over time during a measurement duration at a measurement position.

The time signal generally takes the form of a representation A, or A-scan, which is a time signal for a measurement position, the data of which is noted $x(h,\theta,t)$ or $x(z,t)$. Other representations can of course be defined, such as for example a representation B with a two-dimensional angle/time signal for a given altitude or altitude/time for a given angle.

Another representation will, in particular, also be used for illustration purposes. This is representation C, or C-scan, which is a two-dimensional signal corresponding to the maximum amplitudes (in absolute values) measured for each measurement position:

$$y(h, \theta) = \max_t |x(h, \theta, t)| \text{ or}$$

$$y(z) = \max_t |x(z, t)|$$

Previously discussed FIG. 1 is for example a C-scan.

The ultrasonic waves are propagated as far as the ultrasonic receiving transducer 15. The waves received by the ultrasonic receiving transducer 15 can take several routes, as illustrated in FIG. 2. A first route 16 corresponds to the shortest path for the ultrasonic waves, which in this case corresponds to the surface of the material between the ultrasonic emitting transducer 14 and the ultrasonic receiving transducer 15. This is referred to as lateral waves for the ultrasonic waves propagated at the surface of the material.

Other routes 17 constitute other paths for the ultrasonic waves inside the material, which are diffracted by defect 13 in the direction of the receiving transducer 15. Finally, longest route 18 is the longest path for the ultrasonic waves, which are reflected in the direction of receiving transducer 15 by the opposite surface of the material, in this instance the outer wall 12 of tube 10.

These various routes give rise, in time signal A-scan, to different zones which can be identified. To illustrate this effect, FIG. 3 shows an altitude/time B-scan for a given angle.

Figure 3:
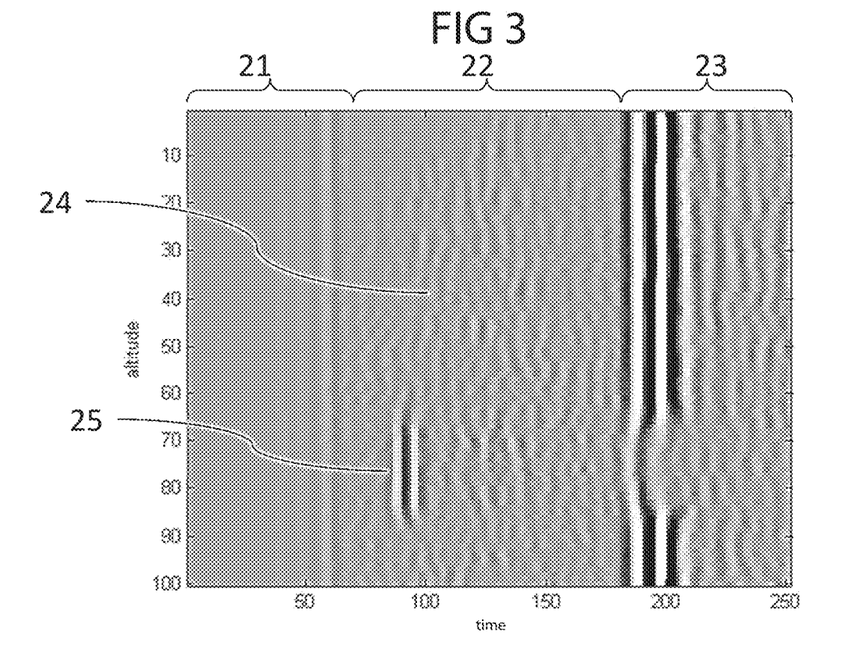
FIG. 3 illustrates an example of a two-dimensional altitude/time representation for a given angle, showing the various portions of a measurement time signal.

In this FIG. 3, a first zone 21 can be identified corresponding to the reception of the ultrasonic waves being propagated at the surface of the material. This is the initial portion of the measurement duration, since these waves have taken the shortest route 16 between the ultrasonic emitting transducer and the ultrasonic receiving transducer. An ultrasonic wave propagated at the surface of the material can thus be designated as a lateral wave. In FIG. 3, this initial portion corresponding to the lateral wave is located within the first sixty time intervals.

A second zone 22 corresponds to the reception of ultrasonic waves being propagated inside the surface of the material which have been diffracted by the material, and in particular by the defects and irregularities inside it. The term "diffraction zone" is used. It is this second zone 22 which is mainly used to detect the defects inside the material.

It is also observed that inside this diffraction zone 22 one finds, for example, portions representative of a structure-borne noise 24, or of portions representative of defects 25.

Third zone 23 corresponds to the background echo, and therefore consists of the ultrasonic waves which have been reflected by the outer surface 12. These are waves which took the longest route 18, and which are therefore logically at the end of the measurement, after the $180^{th}$ time interval.

The invention proposes to use the values taken by the time signals during an initial portion of the measurement duration corresponding to the reception of ultrasonic waves propagated at the surface of the material in order to normalise each time signal overall, to compensate for the influence of the surface irregularities.

To this end, it is proposed for each measurement position to determine a normalisation term from the values taken by the at least one time signal at the measurement position during an initial portion of the measurement duration corresponding to the reception of ultrasonic waves propagated at the surface of the material, and then to normalise the time signal over the measurement duration using the normalisation term to obtain a normalised time signal. The normalisation term is preferably determined from the values taken by time signals of a plurality of measurement positions.

The initial portion of the measurement duration can be defined as containing the data acquired at the start of the measurement until acquisition of the measurements of the lateral waves included in it. It thus contains the measurements of the lateral waves, but possibly other measurements, such as the ultrasonic waves propagated by the shortest route, which can differ from the lateral waves. Indeed, when the surface of the material is flat, as in the example of FIG. 2, the ultrasonic waves propagated by the shortest route in the material are the waves propagating at the surface of the material. The same applies for a concave surface.

Conversely, for a convex surface, ultrasonic waves being propagated directly in the material between the emission position and the reception position arrive before the ultrasonic waves being propagated at the surface of the material. These ultrasonic waves being propagated by a direct route are also measured in the initial portion. In this case the initial portion of the measurement duration corresponding to the reception of ultrasonic waves propagated at the surface of the material covers not only said reception of ultrasonic waves propagated at the surface of the material, but also the prior reception of the ultrasonic waves propagated by the direct route.

The initial portion extends until the time taken by the ultrasonic waves to be propagated at the surface of the material between the emission position 4 and the reception position 5. The initial portion can thus, for example, be a duration shorter than the propagation time of the ultrasonic waves being propagated at the surface of the material between the emission position 4 and the reception position 5, with twice the emission duration added, in order to ensure that all the lateral waves have indeed been received. The duration is therefore taken from the start of the emission. It will also be possible to use measurements made to define the limit chosen for this initial portion, such as for example in FIG. 3, where this initial duration is equal to approximately 60 first time intervals.

To normalise a time signal, one therefore uses not the time signals in their entirety, but only the portions of the time signals corresponding to the initial portion of the measurement duration, corresponding to the reception of ultrasonic waves propagated at the surface of the material, i.e. the reception of the lateral waves. The normalisation terms are not determined from the subsequent portions of the time signals. In particular, the normalisation terms are not determined from the portions of the measurement duration corresponding to the reception of ultrasonic waves the propagation path of which is longer than the propagation at the surface of the material.

There can, therefore, be a prior step of selection or extraction of the portion of time signals corresponding to the initial portion of the measurement duration, by deleting from the data used for this normalisation the measurements which follow, chronologically, the reception of ultrasonic waves propagated at the surface of the material, i.e. on reception of the lateral waves.

The normalisation term can be determined from the temporally average power of the values taken by the time signal during the initial portion of the measurement duration corresponding to the reception of ultrasonic waves propagated at the surface of the material. For example, for a measurement position, the square of the normalisation term can be proportional to the temporally average power of the values taken by the time signal during the initial portion of the measurement duration corresponding to the reception of ultrasonic waves propagated at the surface of the material.

If the normalisation term for a measurement position z is noted C(z), this therefore gives, for example:

$$C^2(z) \propto \frac{1}{N_{lateral\,wave}} \sum_{t \in lateral\,wave} x^2(z, t)$$

where $N_{lateral\,wave}$ is the number of measurements belonging to the initial portion of the measurement duration corresponding to the reception of ultrasonic waves propagated at the surface of the material.

It should be noted that the temporally average power of the lateral wave $P_{OL}(z)$ is equal to:

$$P_{OL}(z) = \frac{1}{N_{lateral\,wave}} \sum_{t \in lateral\,wave} x^2(z, t)$$

Although such a normalisation term determined from the temporally average power of the amplitude values can be used to normalise directly the time signal of the corresponding measurement position, a relatively strong variability of this normalisation term can be observed, in particular due to the structure-borne noise.

The normalisation term is thus preferably determined from the values taken by time signals of a plurality of measurement positions. Spatial filtering corresponding to measurement positions distributed over a portion of the surface of the material can be used to filter the normalisation term of a measurement position belonging to said surface portion. A median spatial filter is thus for example applied, i.e. one constructed from the median of the values in question, in the form of a sliding window. The average could also be used, but the median is preferred to the average to prevent smoothing any sudden sticking variations. The filter's window must be sufficiently large to reduce the noise appreciably, and sufficiently small so as not to mask small local sticking variations. For example, one can take a window of a size of between 5 mm and 20 mm and between 15 degrees and 35 degrees (for a tube, with the intervals mentioned above).

Figure 4:
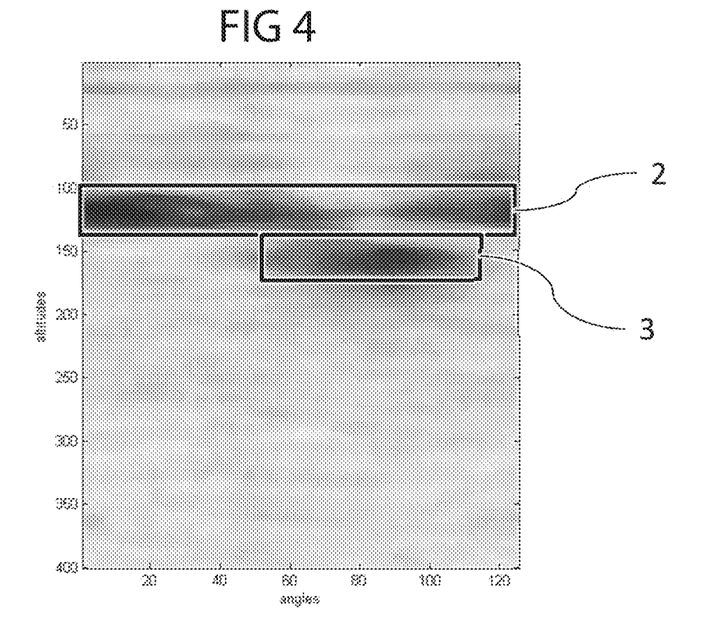
FIG. 4 shows a map of terms of normalisation for the example of FIG. 1 in one possible embodiment of the invention.

FIG. 4 shows a map of the normalisation terms obtained in this manner for the example of FIG. 1, with the lowest values shown as dark, and the highest values shown as bright. This contains, in black frames 2 and 3, the zones where the surface irregularities cause a coupling fault. The low values taken by the normalisation terms in these zones, and conversely the higher values of the normalisation terms, enable the small amplitude of the time signals affected by the coupling faults to be compensated. These normalisation terms can be used to normalise the A-scan time signals, for example by dividing their values by the normalisation terms.

Figure 5:
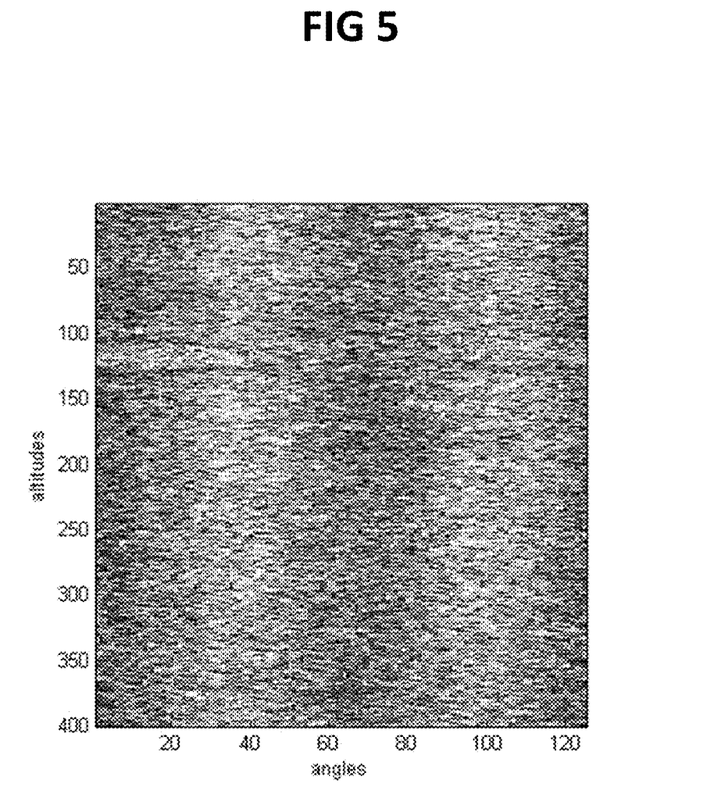
FIG. 5 shows a map illustrating the maximum values of the time signals normalised for a plurality of measurement positions in one possible embodiment of the invention, using the example of FIG. 1.

FIG. 5 is a C-scan showing the result of the normalisation of the A-scans used for FIG. 1 by the normalisation terms determined as in the example following their spatial filtering, restricted to the portion corresponding to the diffraction zone, and therefore representative of the structure-borne noise. One can observe the great attenuation of the irregularities due to the coupling faults, which had been identified in black frames 2, 3 in FIG. 1.

To determine the normalisation term for a measurement position, the propagation time of the ultrasonic waves corresponding to said measurement position can also be used. Once again, in this case, the time signals of a plurality of measurement positions during the initial portion of the measurement duration corresponding to the reception of the ultrasonic waves propagated at the surface of the material are used.

To this end the propagation times between emission position 4 and corresponding reception position 5 are determined for the ultrasonic waves for each measurement position. The propagation time at a measurement position can be determined by correlating the time signal with a reference signal representative of the reception of an ultrasonic wave propagated along the shortest route in the inspected zone. This route can, for example, be at the surface of the material, in which case the reference signal is representative of the reception of an ultrasonic wave propagated at the surface, or alternatively can be a direct route in the material, in particular if the surface is convex, in which case the reference signal is representative of the reception of an ultrasonic wave propagated by this direct route.

This reference signal can, for example, be an ideal theoretical signal, or one calculated by simulation. It is also possible to define it empirically from a set of measurements corresponding to the reception of lateral waves. One can, for example, take the spatially average values of a set of previously acquired reception measurements of ultrasonic waves in order to define the reference signal.

The correlation peak corresponds to the reception of an ultrasonic wave, and therefore, if the moment of the emission pulse of the ultrasonic wave is known, enables the propagation time of this ultrasonic wave to be determined. In addition to the moment of the emission pulse, all other time references which are fixed in relation to the moment of the emission pulse can be used. This reference can, in particular, be the start of the measurement duration if its time position is fixed relative to the moment of the emission pulse.

Figure 6:
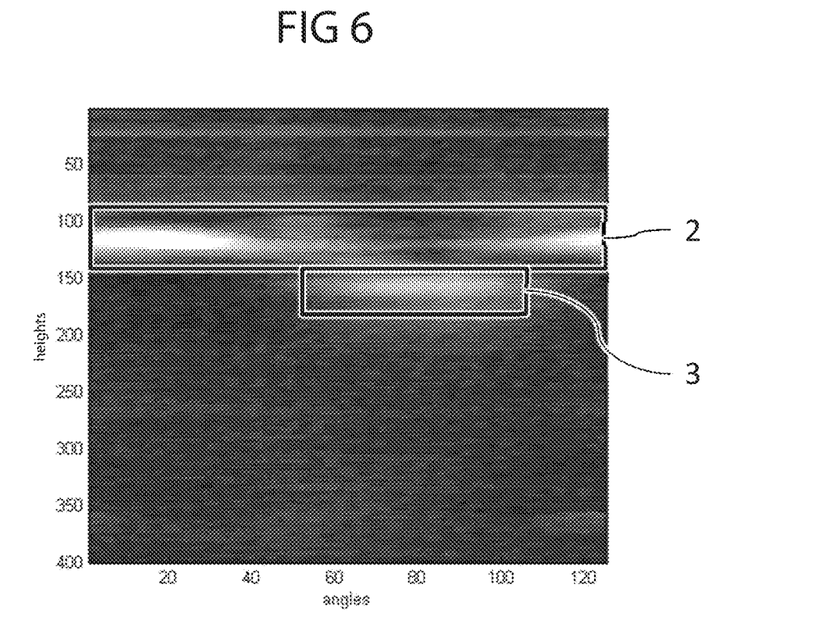
FIG. 6 shows a map of propagation times for the ultrasonic waves, using the example of FIG. 1.

FIG. 6 thus shows a propagation time map produced for the example illustrated by FIG. 1, with the shortest route times shown as dark and the longest route times shown as bright. This contains, in black frames 2 and 3, the zones where the surface irregularities cause a coupling fault. It is therefore observed that the surface irregularities can be brought to light by means of the propagation times, and that it is therefore possible to use the latter to normalise the time signals in order to compensate for the influence of the coupling faults.

As an example, it is possible to use a relationship between the propagation time of the lateral wave and the power received via the lateral wave to determine the normalisation term. It is thus possible to construct normalisation term $C(z)$ for measurement position z from the temporally average power of the lateral wave.

More specifically:
for each time grouping of a plurality of propagation time groupings one determines the temporally average power, for measurement positions with a propagation time belonging to said time grouping, of the values taken by the time signal during the initial portion of the measurement duration corresponding to the reception of ultrasonic waves propagated at the surface of the material, and the normalisation term of a measurement position is determined from the temporally average powers of the measurement positions of the propagation time grouping corresponding to the propagation time of the measurement position.

In particular, the normalisation term of a measurement position can be determined from the average of the temporally average powers of the measurement positions of the propagation time grouping corresponding to the propagation time of the measurement position.

One thus obtains, firstly, a corrected temporally average power which associates an average power with each time grouping:

$$P_{OL,corrected}(t) = \frac{1}{N_t} \sum_{z | t_{OL}(z)=t} P_{OL}(z)$$

where $N_t$ is the number of measurement positions for which the propagation time of the lateral wave belongs to the measurement grouping of time t, and where $$P_{OL}(z) = \frac{1}{N_{lateral\,wave}} \sum_{t \in lateral\,wave} x^2(z, t)$$

The corrected temporally average power $P_{OL,\,corrected}$ is then used to determine normalisation term $C(z)$:

$$C(z) = \sqrt{P_{OL,corrected}(t | t_{OL}(Z)=t)}$$

Figure 7:
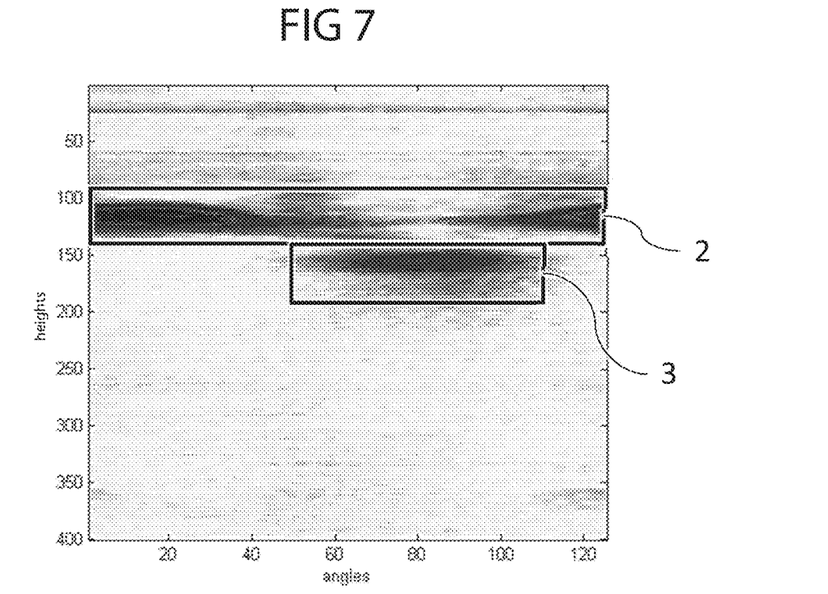
FIG. 7 shows a map of the terms of normalisation for the example of FIG. 1 in one possible embodiment of the invention.

FIG. 7 shows a map of the normalisation terms obtained in this manner for the example of FIG. 1, with the lowest values shown as dark, and the highest values shown as bright. This contains, in black frames 2, 3, the zones where the surface irregularities cause a coupling fault, which had already been revealed with the propagation times map illustrated by FIG. 6. The low values taken by the normalisation terms in these zones, and conversely the higher values of the normalisation terms elsewhere, enable the small amplitude of the time signals affected by the coupling faults to be compensated.

As above, these normalisation terms can be used to normalise the A-scan time signals, for example by dividing their values by the normalisation terms.

In addition, as above, spatial filtering corresponding to measurement positions distributed over a portion of the surface of the material can be used to filter the normalisation term of a measurement position belonging to said surface portion.

When the time signal has been normalised a known method of defect detection can then be used, for example by comparing the normalised values with thresholds, or by using more elaborate methods which not only enable the defects to be detected, but also to be characterised.

In particular, it is possible to construct one of the mentioned representations, typically a C-scan, from normalised time signals restricted to the diffraction zone, i.e. to the measurement duration corresponding to the reception of ultrasonic waves propagated inside the material, excluding lateral waves or background echoes, and then from this representation to detect the defects by an analysis of the values of this representation.

The described method is typically implemented by a computer with a processor and a memory. To this end a computer program product is proposed including program code instructions for execution of the method according to the invention when said program is executed on a computer.

The invention is not limited to the embodiment described represented in the appended figures. Modifications are also possible, particularly from the standpoint of the constitution of the various elements, or by substitution of technical equivalents, without however going beyond the invention's field of protection.

The invention claimed is:

1. Method of ultrasound detection of defects in a material, comprising the following steps, for a plurality of pairs of emission position and reception position:
- emission of ultrasounds from an ultrasonic emitting transducer placed against the material at an emission position,
- acquisition, by an ultrasonic receiving transducer placed against the material in the reception position corresponding to said emission position, of at least one time signal representative of the amplitude of the ultrasounds propagated in the material over time during a measurement duration at a measurement position, wherein the method includes the following steps:
- for each measurement position, determination of a normalisation term of said measurement position using the values taken by at least the time signal in said measurement position during an initial portion of the measurement duration corresponding to the reception of ultrasonic waves propagated at the surface of the material;
- for each measurement position, normalisation of the time signal at said measurement position in relation to measurement duration using the normalisation term of said measurement position determined from the at least one time signal at said measurement position to obtain a normalised time signal;
- processing of normalised time signals for different measurement positions to detect defects in the material.

2. The method according to claim 1, wherein the ultrasounds are emitted by the ultrasonic emitting transducer during a pulse duration, and the initial portion of the measurement duration is a duration shorter than the propagation time of the ultrasonic waves propagating at the surface of the material between the emission position and the reception position with twice the pulse duration added, where the duration is measured from the start of the pulse.

3. The method according to claim 1, wherein the normalisation term is determined from the temporally average power of the values taken by the time signal during the initial portion of the measurement duration corresponding to the reception of ultrasonic waves propagated at the surface of the material.

4. The method according to claim 3, wherein, for a measurement position, the square of the normalisation term is proportional to the temporally average power of the values taken by the time signal during the initial portion of the measurement duration corresponding to the reception of ultrasonic waves propagated at the surface of the material.

5. The method according to claim 1, further including the determination of the propagation times between the emission position and the corresponding reception position for ultrasonic waves, and wherein the normalisation term for a measurement position is determined from the propagation times at different measurement positions.

6. The method according to the previous claim 5, wherein the propagation time at a measurement position is determined by correlating the time signal with a reference signal representative of the reception of an ultrasonic wave.

7. The method according to claim 5, wherein:
- for each time grouping of a plurality of propagation time groupings the temporally average power is determined, for measurement positions with a propagation time belonging to said time grouping, of the values taken by the time signal during the initial portion of the measurement duration corresponding to the reception of ultrasonic waves propagated at the surface of the material, and
- the normalisation term of a measurement position is determined from the temporally average powers of the measurement positions of the propagation time grouping corresponding to the propagation time of the measurement position.

8. The method according to claim 7, wherein the normalisation term of a measurement position is determined from the average of the temporally average powers of the measurement positions of the propagation time grouping corresponding to the propagation time of the measurement position.

9. The method according to claim 1, wherein spatial filtering corresponding to measurement positions distributed over a surface portion of the material is used to filter the normalisation term of a measurement position belonging to said surface portion.

10. A non-transitory computer-readable medium including program code instructions stored thereon for execution of the method according to claim 1 when said non-transitory computer-readable medium is read by a computer.

* * * * *